United States Patent
Thurner (10) Patent No.: US 12,128,276 B2
(45) Date of Patent: Oct. 29, 2024

(54) SYSTEMS AND METHODS FOR AUTOMATED EVALUATION AND UPDATING OF GOLF SCORE INDICES

(71) Applicant: Cap Patrol, Covington, KY (US)

(72) Inventor: George Thurner, Covington, KY (US)

( * ) Notice: Subject to any disclaimer, the term of this patent is extended or adjusted under 35 U.S.C. 154(b) by 262 days.

(21) Appl. No.: 17/695,357

(22) Filed: Mar. 15, 2022

(65) Prior Publication Data

US 2022/0296964 A1 Sep. 22, 2022

Related U.S. Application Data (60) Provisional application No. 63/161,780, filed on Mar. 16, 2021.

(51) Int. Cl.
| | |
|---|---|
| *A63B 69/36* | (2006.01) |
| *A63B 24/00* | (2006.01) |
| *A63B 71/06* | (2006.01) |
| *G06N 3/08* | (2023.01) |

(52) U.S. Cl.
CPC ...... *A63B 24/0062* (2013.01); *A63B 69/3605* (2020.08); *A63B 71/0669* (2013.01); *G06N 3/08* (2013.01); *A63B 2024/0068* (2013.01); *A63B 2220/12* (2013.01); *A63B 2220/62* (2013.01)

(58) Field of Classification Search
CPC ............ A63B 71/0669; A63B 69/3605; A63B 2024/0068
See application file for complete search history.

(56) References Cited

U.S. PATENT DOCUMENTS

| | | | | |
|---|---|---|---|---|
| 2004/0007617 | A1* | 1/2004 | Shaw, Jr. ........... | A63B 71/0669 235/380 |
| 2008/0167737 | A1* | 7/2008 | Schmidt ............ | A63B 71/0669 700/92 |
| 2011/0230985 | A1 | 9/2011 | Niegowski et al. | |
| 2012/0296456 | A1* | 11/2012 | Jentz ................. | G06Q 10/0639 700/93 |

(Continued)

OTHER PUBLICATIONS

International Search Report and Written Opinion issued in PCT Application No. PCT/US22/20496, dated Jun. 15, 2022 (765697.000004).

*Primary Examiner* — Jay Trent Liddle
(74) *Attorney, Agent, or Firm* — Hogan Lovells US LLP (57) ABSTRACT

Electronic content, including that obtained via software applications executing on client devices, pertaining to golfers' handicap indices and scoring is automatically obtained by golf clubs and other courses. Such player data can be electronically monitored and analyzed in real-time in accordance with expected score qualities and guidelines in the sport. In particular, one or more algorithms may be routinely executed to look for various data point indicators which may mean a player is manipulating his or her handicap index. The systems and methods can objectively generate an overall score for every participating player, based at least in part on deduction of points for data determined abnormal based on expected qualities. Should a player's overall score reach a predetermined flagging level, the systems and methods automatically adjust the player's handicap to promote fair play. Machine learning schema can assist in tasks such as scoring analyses and automated handicap adjustments.

20 Claims, 3 Drawing Sheets

(56) References Cited

U.S. PATENT DOCUMENTS

| | | | |
|---|---|---|---|
| 2012/0322582 A1* | 12/2012 | Solheim | A63B 69/36 |
| | | | 473/131 |
| 2013/0331969 A1* | 12/2013 | Piercy | A63B 71/0697 |
| | | | 700/92 |
| 2016/0158640 A1* | 6/2016 | Gupta | A63F 13/812 |
| | | | 463/3 |
| 2016/0228757 A1 | 8/2016 | Rhule et al. | |
| 2018/0200605 A1* | 7/2018 | Syed | A63B 69/3605 |
| 2019/0060759 A1 | 2/2019 | Krishnamurthy | |
| 2019/0192951 A1* | 6/2019 | Rojas | G06F 21/64 |
| 2020/0269139 A1 | 8/2020 | Aghdaie et al. | |
| 2020/0298094 A1 | 9/2020 | Syed et al. | |
| 2021/0086089 A1 | 3/2021 | Pardeshi et al. | |

\* cited by examiner

SYSTEMS AND METHODS FOR AUTOMATED EVALUATION AND UPDATING OF GOLF SCORE INDICES

CROSS-REFERENCE TO RELATED APPLICATION

This application claims the benefit of U.S. Provisional Patent Application No. 63/161,780, filed 16 Mar. 2021, which is incorporated by reference herein in its entirety.

BACKGROUND

In the sporting field of amateur golf, scores from various previously-played rounds may be utilized to determine a "handicap" for a particular player. The handicap is a familiar numerical value indicative of the skill and performance of the player over the history of his or her previous play. In instances where golfers of varying degrees of abilities are matched against each other, player handicaps may be utilized to adjust the scores of the players in such a way to allow the players of different skill levels to compete on a more even level. For example, final scores may be adjusted to allow a player that scores a 72 in a round of golf, to be compared to another player who scores an 80 for the same round, but is less proficient than the other player. However, because scores are often self-reported, a player may manipulate his or her scores to appear to have a higher (e.g., "worse") handicap than what is accurate. By having a higher handicap not reflective of the playing ability of the player, that player may have an advantage in competitive tournaments, including the many with substantial monetary prizes. Thus, a player has incentive to understate scores for rounds, to artificially inflate a handicap and to play exceptionally better than what is evidenced by the player's handicap.

BRIEF DESCRIPTION OF THE DRAWINGS

Various embodiments in accordance with the present disclosure will be described with reference to the drawings, in which.

DETAILED DESCRIPTION

Systems and methods in accordance with various embodiments of the present disclosure may overcome one or more of the deficiencies in reporting of scores for rounds of golf, to reduce cheating and ensure that a player is not overly inflating his or her handicap to gain benefit when playing other golfers, as part of compliance with applicable rules such as those of the World Handicap System ("WHS"). Applying unique, technical-based analyses at capacities and speeds beyond mere human examination of golf scores, the present systems and methods determine, based on historical performance information such as past scores and handicaps, a measure that is indicative of likelihood that the player (also referred herein as a "user") is incorrectly reporting one or more past scores. The systems and methods may include a component that identifies when the player is supposed to be reporting a score (i.e., keeping track of games played and scores reported) as well as analyzes the reported scores to determine whether the player is accurately reporting scores or reporting erroneous numbers. Thus, a player can be warned, disqualified, or investigated further in instances where cheating is likely.

Figure 1:
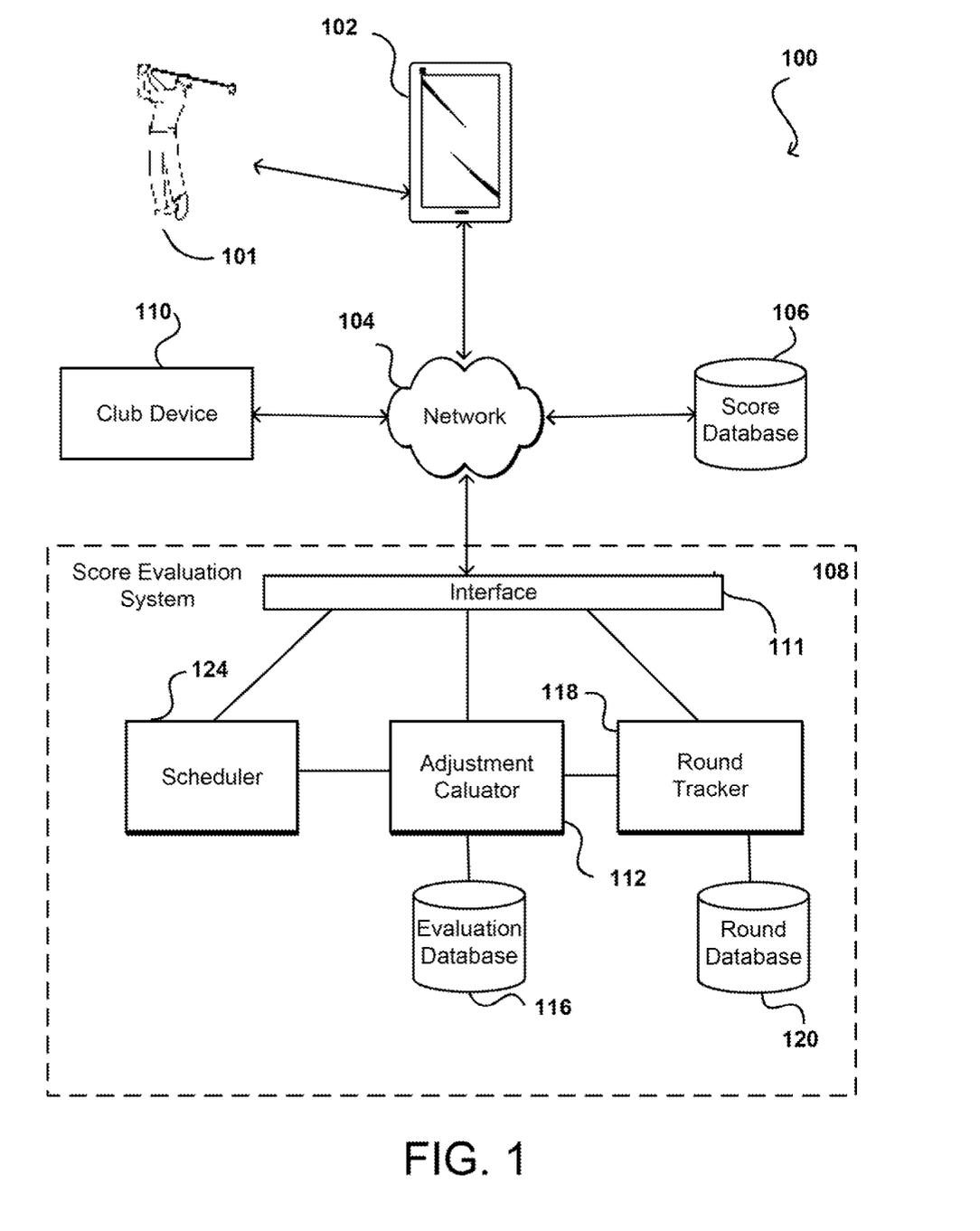
FIG. 1 is an example environment in which various illustrative embodiments described herein may be implemented.

Referring to FIG. 1, an illustration of an environment for automated reporting and analyzing golf scores is provided. The environment 100 includes a score evaluation system 108 that receives scores from player 101 and determines a likelihood that the user has not reported one or more accurate scores. The users may provide information via one or more client computing devices 102. Further, the environment 100 includes a club device 110 that may be utilized to monitor player performance and evaluations as well as provide additional scoring or other information related to a particular golfing club (be it a country club or public course) and its players or members. The computing device 102 and the club device 110 may communication with the score evaluation system 108 via a network 104. The network(s) can include any appropriate network, such as the Internet, a local area network ("LAN"), a cellular network, an Ethernet, or other such wired and/or wireless network.

Communication with the score evaluation system 108 may be through an interface, such as interface 110. As known for network environments, the interface layer can include components such as interfaces (e.g., application programming interfaces or "APIs"), load balancers, request and/or data routers, and the like. Additionally, the software applications can include one or more graphical user interfaces ("GUIs") to serve as a communication interface between the player and one or more APIs, including those interfacing with vendor systems. The GUIs can also include instructions for converting data in various formats, such as third-party scoring, into a format for use and presentation by the GUIs.

The environment 100 further includes a scoring database 106, such as one containing WHS data. Although described herein as a particular database, any number of other databases or data stores having player scores which may be utilized to populate the system. The scoring database 106 includes publicly available scoring information for members. For example, scoring database 106 may include a series of rounds played by Player A, as well as a calculated handicap. Calculating a handicap is known in the art and will not be described in greater detail herein. In some embodiments, one or more components of the score evaluation system 108 may scrape the utilized information from an interface to the WHS database 106 (e.g., from a webpage displaying player scores and handicaps) and provide the scoring information to one or more components of the score evaluation system 108.

Score evaluation system 111 can include a scheduler 124 permitting a player to schedule a round of golf. The score for that round of golf may then be utilized to provide the system 108 with additional information allowing evaluation of the player's current handicap and determine a measure of likelihood of the calculated handicap being accurately reported. The user may utilize computing device 102 and/or club device 110 to schedule a game for a particular time and location. For example, Player A may schedule a first round of golf at 8:00 o'clock on a Monday morning and a second round of golf on Tuesday afternoon at 1:00 o'clock.

Scheduler 124 keeps track of unplayed rounds and may provide round tracker 118 with an indication of an anticipated round. For example, for Player A's round scheduled for 8:00, scheduler 124 may verify that the round has been played and provide round tracker with an indication that the round was played and to expect a score for the round. Round tracker 118 may send one or more notifications to a player via device 102 to remind the player or prompt the player to enter a score for a played round. Round tracker 118 may then store the score information in round database 120.

In this vein, the vast majority of golf clubs employ a tee time booking system from a third party software company, allowing players to reserve a time to play golf at a given course. The present systems and methods may be configured to, automatically or manually, obtain and/or share such booking information, such as who is playing with whom, on a particular day, and at what location. This procurement and sharing of data may be accomplished by techniques including scrapping or using an API connection.

Of note, some of the third-party tee time software offerings may, based on reserved tee time data, access a scoring database, such as the WHS handicap system, to verify whether a given player submitted a score for his or her reserved round. While that third-party access scheme permits a club to ensure that all players are turning in their scores per WHS handicap guidelines, a problem arises in that a player can turn in any score whatsoever, as no one other member of that tee time playing group can view scores submitted by other players; so a player could turn in all of his or her scores and appear to comply with requisite guidelines, but that player, in an attempt to cheat, could be turning in incorrect scores which are higher that what was actually shot, thereby boosting the player's handicap to a level higher than it should be.

The present systems and methods address this area of concern by, not only electronically checking scores and confirming that they are submitted (such as to the WHS system), but also automatically notifying, potentially, via one or more software applications including one or more executing on a player computing device 102, each player in a given grouping on a given day what each player turned in as a score for the round played together. This provides the club with a device-based "peer review" to confirm every score turned in at that club. In some embodiments, such peer review data is provided to the applicable club on a daily basis.

More particularly, in some illustrative embodiments, the subject systems and methods, after identifying a user request for a tee time, can ascertain that a predetermined amount of time (such as a calculated average time for a golfer to play nine or eighteen holes of golf) has passed since the scheduled tee time. In addition, or alternatively, a user's round status can be tracked using geolocation features of one or more software applications or even by tracking equipment embedded or affixed to golf clubs (drivers, putters, etc.) or other equipment. Further, a club can enter handicap numbers or other identifying information for guests visiting that club for, say, a tournament, and any reporting and player updating for purposes of the present systems and methods can be electronically shared with the visiting players' home club and various databases.

As noted, in accordance with various features of the present disclosure, identifying information for the user is electronically transmitted, with such information showing past golfing performance. Adjustment calculator 112 may then, including when triggering via automated system updates and/or notifications, determine the likelihood that a player is reporting accurate scoring results. The adjustment calculator 112 can access one or more of varied score database(s) which may include reported rounds of a player, as well as information that has been retrieved from the scoring database 106. Once a sufficient number of rounds are received for a player, new scores may be evaluated to determine a likelihood that a given score is correctly reported. One or more rules or characteristics of previous scores may be utilized to determine a likelihood measure. By way of non-limiting examples, and as discussed below, changes in handicap over a period of time, play at a home course (versus another course), and performance in tournament play all fall within the rubric of "historical performance data" herein and may be taken into account when calculating an accuracy likelihood measure for a given score. For the avoidance of doubt, the term "historical performance data" is open-ended by design and may encompass any number of measures of golfing performance.

In some embodiments, one or more factors for determining a likeliness score may be weighted to contribute differently to the overall likelihood measure. For example, because pressure is often greater in tournament play as opposed to more casual play, scores from tournaments may be weighted less significantly to reflect, for example, what are higher scores because of the pressure. Thus, the likelihood score measures overall performance and is not adversely affected by instances where a player did not perform as expected in a given circumstance.

One or more neural networks may be employed to develop a trained model for analysis of scores, as part of adjustment calculator 112 or otherwise, and determining whether a score is anomalous and/or whether an anomalous score potentially attributable to cheating. For example, verified scores may be provided to a neural network, along with one or more incorrect scores. The neural network may evaluate the scores and be trained to select those scores which do not reflect the playing ability attributed to the rest of the accurate scores. Thus, once trained with information regarding a score and any circumstances in which the round was played, the neural network can apply one or more models to determine a measure of how likely a given score is incorrect. Once evaluated, scores and likelihood measure may be stored in evaluation database 116 for further analysis.

As noted, neural network, deep learning, and other machine learning techniques have applications for present purposes. As is known in the neural network and artificial intelligence arts, a variety of neural network types could be applied, including, but by no means limited to, feedforward, recurrent, modular, and self-organizing neural networks. Prior to production environment use, a non-production sample data set of typical golf scoring content may be employed for training a neural network model for processing and analysis of scores. Metrics (including confidence scoring), derived through machine learning, may assist the present systems and methods in tracking and understanding patterns in golf scores. Although graphics processing units ("GPUs") are effective for many deep learning neural network applications, the present systems and methods can be used with GPU-based or central processing unit ("CPU")-based systems.

More particularly, with the emergence of the deep convolutional neural network ("CNN"), a programming and information processing paradigm allowing a machine to learn from data, object detection performance has improved significantly. CNNs are a family of statistical learning models used in machine learning applications to estimate or approximate functions which depend on a large number of inputs. The various inputs are interconnected with the connections having numeric weights that can be tuned over time, enabling the networks to be capable of "learning" based on additional information. Different layers of the network can be composed for different purposes. There is an input layer, which along with a set of adjacent layers, forms the convolution portion of the network. The bottom layer of the convolution layer, along with a lower layer and an output layer, makes up the fully-connected portion of the network. A number of output values can be determined from the output layer, which can include several items determined to be related to an input item, among other such options.

Any type of neural network employed in connection with the present disclosure will likely need tweaking and/or additional or alternative elements to fit the specifics of particular situations. In certain embodiments, training a CNN may involve significant use of computation resources and time, such that this may correspond to a preparatory step to servicing content display requests and/or performed relatively infrequently with respect to request servicing and/or according to a schedule. As known in the object-oriented and other computer science arts, the machine learning features hereunder may be accomplished through the use of separate software modules executing on top of a feature map.

In instances where a likelihood measure for a score exceeds a threshold, including one predetermined in accordance with the present disclosure, a notification may be sent to club device 110 for further analysis, including that by one or more humans. For example, if a score, or a trend seen in multiple scores, indicates a high likelihood of cheating by a player, that player's club may be notified via club device 110. The scores may then be reevaluated and, in the case where cheating is confirmed, action can be taken by the club to prevent future incidents of impropriety. This may include, for example, updating and/or recalculating a player handicap or suspending play for the user. The various systems and methods can be configured to present and export data in spreadsheet form, to facilitate both machine and human analyses.

As to particulars of the data automatically obtained and processed for score accuracy likelihood analyses and the like, it is open-ended by design, and algorithms in various embodiments can consider various data types and fields. In illustrative embodiments, algorithms can include and consider one or more of the following rules, with one or more being weighted: a high-and-low index (to show playing potential based on a select period of time, such as a recent history comprised of one year); home-and-away scoring (as it is challenging for a club to track members' play at other courses, and an indication a player is managing his or her handicap by submitting scores outside of the norm at away courses, consideration is given to scores for players of a similar ability score at an alternate course); a player potential index (as playing under pressure, by the rules of the sport, and having scores attested is one of the best indicators of potential, the systems and methods can examine a player's tournament data over a set period and calculate a factor based on potential); round scores submitted (monitoring when a player plays a round of golf, a check is performed to see if a score is turned in for that round, as an indicator of whether the player is recording his play for every opportunity, and/or also monitoring "peer review" data as discussed herein); and particular tournament scoring models such as the Knuth Tournament Point System™ (which, in general, adjusts a player's tournament handicap for future events, based on an awarding of points for first through fifth-place finishes at events over the previous two years).

After gathering and analyzing the selected data, some embodiments of the systems and methods hereunder automatically determine an overall handicap baseline score every player. Such an overall score may include a deduction for data points out of the norm. When a given player's overcall score reaches a predetermined level, the systems and methods can flag that player's account for a handicap adjustment, such as that performed by adjustment calculator 112, in the interest of promoting fair play.

The present systems and methods may further be configured to include one or more features relating to lawful wagering. Round data automatically stored and shared, with user permission via one or more software applications executing on computing device 102, permits players to ascertain who owes amount to other plays, pursuant to friendly bets. Players can thus also enter into formal, lawful, or token friendly, wagers against players against whom they are not competing on a given day.

Figure 2:
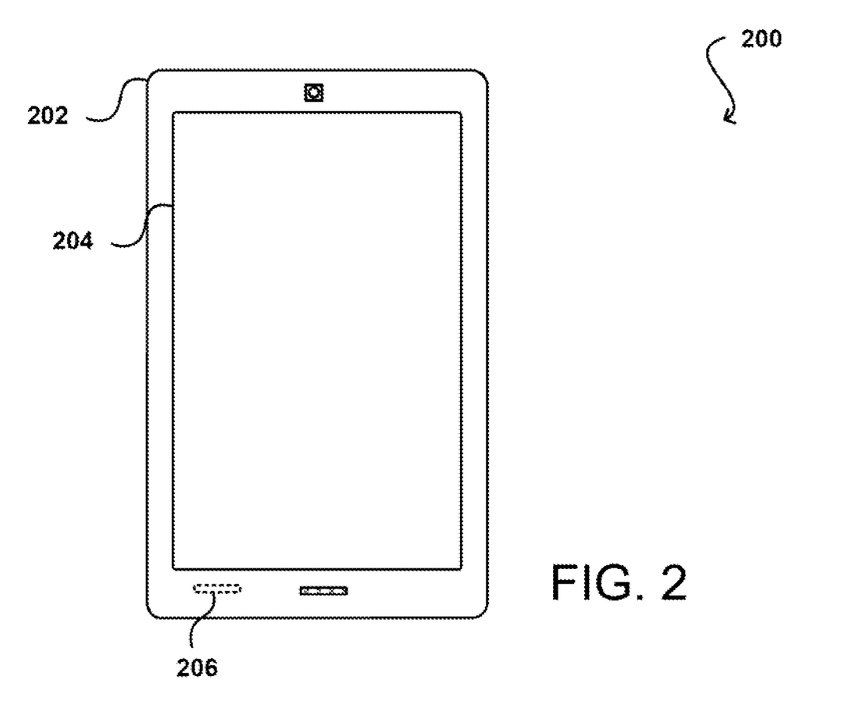
FIG. 2 illustrates a computing device that can be utilized in accordance with various embodiments.

FIG. 2 illustrates an example computing device 200 that can be used in accordance with various embodiments. Although a portable computing device (e.g., a smart phone, an electronic book reader, or tablet computer) is shown, it should be understood that any device capable of receiving and processing input can be used in accordance with various embodiments discussed herein. The devices can include, for example, desktop computers, notebook computers, electronic book readers, personal data assistants, cellular phones, video gaming consoles or controllers, wearable computers (e.g., smart watches or glasses), television set top boxes, and portable media players, among others. In this example, the computing device 200 has a display screen 204 and an outer casing 202. The display screen under normal operation will display information to a user (or viewer) facing the display screen (e.g., on the same side of the computing device as the display screen). In line with the disclosure herein, the device can internally include one or more communication components 206.

Figure 3:
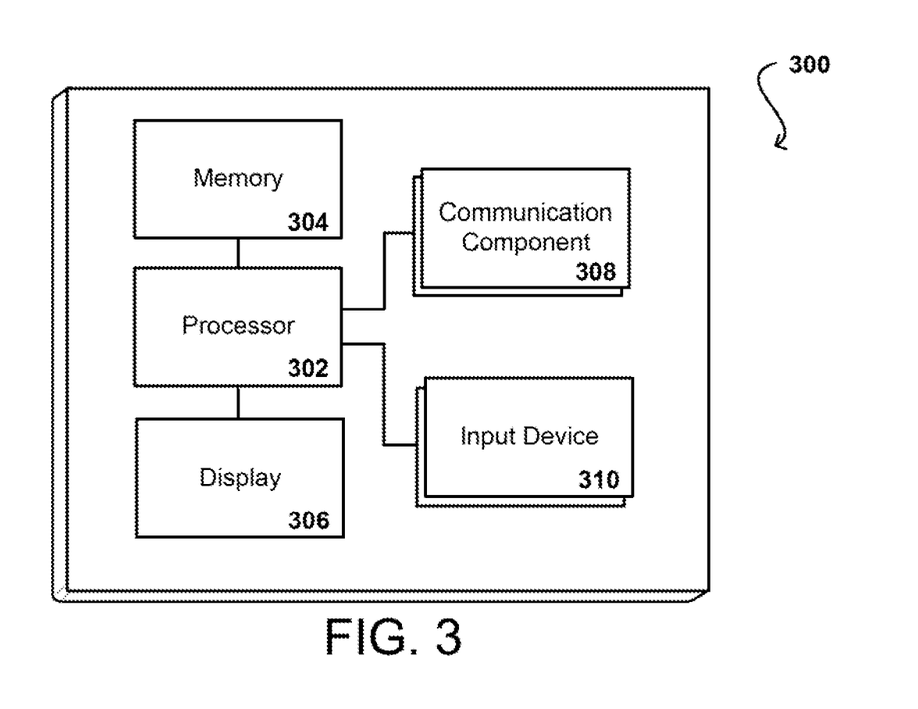
FIG. 3 illustrates an example configuration of components of a computing device, such as the device illustrated in FIG. 2.

FIG. 3 illustrates a set of basic components of a computing device 300 such as the device 200 described in connection with FIG. 2. In this example, the device includes at least one processor 302 for executing instructions that can be stored in a memory device or element 304. As would be apparent to one of ordinary skill in the art, the device can include many types of memory, data storage or computer-readable media, such as a first data storage for program instructions for execution by the at least one processor 302, the same or separate storage can be used for images or data, a removable memory can be available for sharing information with other devices, and any number of communication approaches can be available for sharing with other devices. The device typically will include at least one type of display element 306, such as a touch screen, electronic ink ("e-ink"), organic light emitting diode ("OLED") or liquid crystal display ("LCD"), although devices such as portable media players might convey information via other means, such as through audio speakers. The device can include at least one communication component 308, as may enabled wired and/or wireless communication of voice and/or data signals, for example, over a network such as the Internet, a cellular network, a Wi-Fi network, BLUETOOTH®, and the like. The device can include at least one additional input device 310 able to receive conventional input from a user. This conventional input can include, for example, a push button, touch pad, touch screen, wheel, joystick, keyboard, mouse, trackball, camera, microphone, keypad or any other such device or element whereby a user can input a command to the device. These I/O devices could even be connected by a wireless infrared or Bluetooth or other link as well in some embodiments. In some embodiments, however, such a device might not include any buttons at all and might be controlled only through a combination of visual and audio commands such that a user can control the device without having to be in contact with the device.

Figure 4:
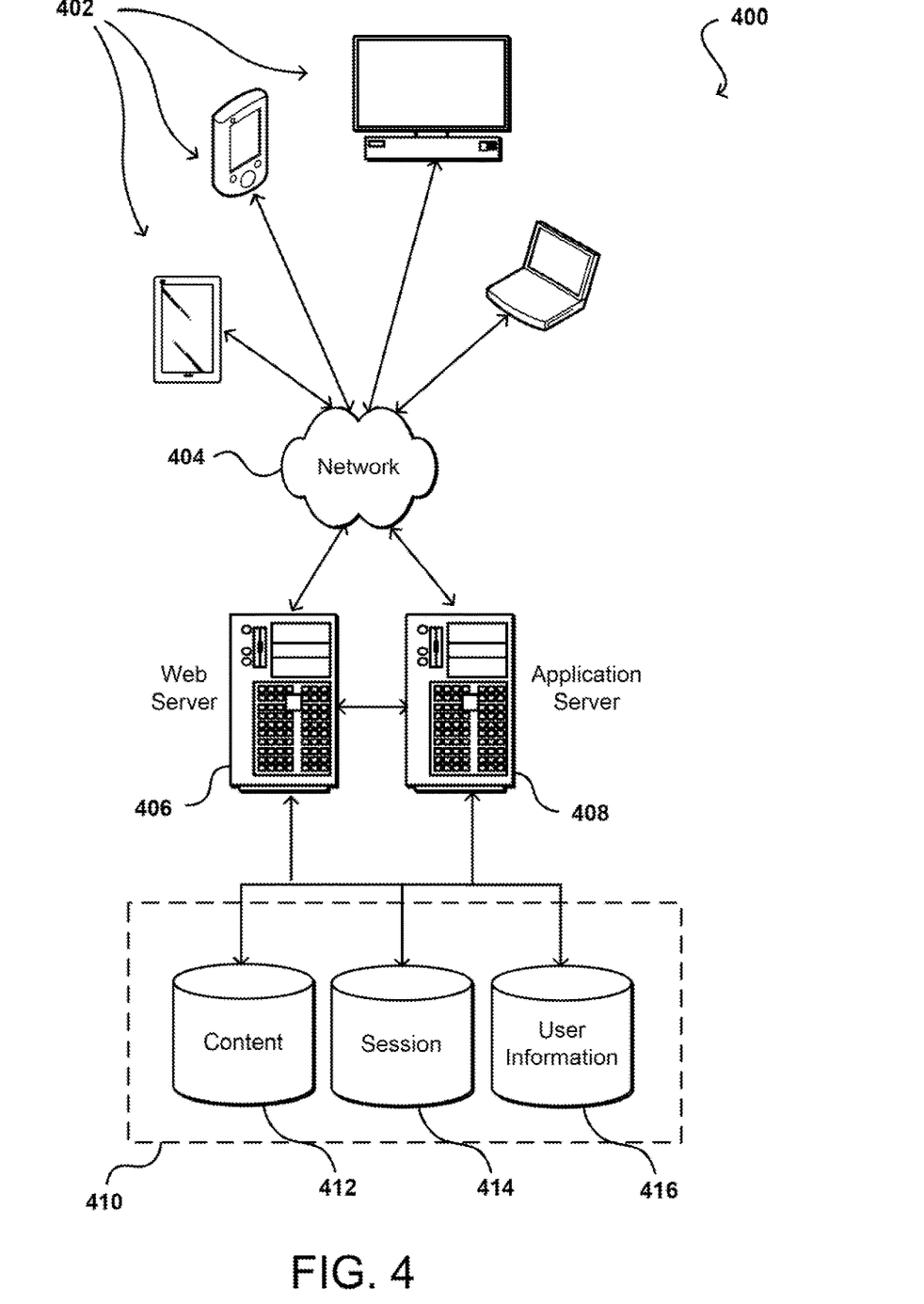
FIG. 4 illustrates an example environment in which aspects of the various embodiments can be implemented.

As discussed, different approaches can be implemented in various environments in accordance with the described embodiments. For example, FIG. 4 illustrates an example of an environment 400 for implementing aspects in accordance with various embodiments. As will be appreciated, although a Web-based environment is used for purposes of explanation, different environments may be used, as appropriate, to implement various embodiments. The system includes one or more electronic client devices 402, which can include any appropriate device operable to send and receive requests, messages or information over an appropriate network 404 and convey information back to a user of the device. Examples of such client devices 402 include personal computers, cell phones, handheld messaging devices, laptop computers, set-top boxes, personal data assistants, electronic book readers and the like. The network 404 can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server 406 for receiving requests and serving content in response thereto, although, for other networks, an alternative device serving a similar purpose could be used, as would be apparent to one of ordinary skill in the art.

The illustrative environment includes at least one application server 408 and at least one data store 410. It should be understood that there can be several application servers, layers or other elements, processes or components, which may be chained or otherwise configured, which can interact to perform tasks such as obtaining data from an appropriate data store. As used herein, the terms "data store" and "database" refer to any device or combination of devices capable of storing, accessing and retrieving data, which may include any combination and number of data servers, databases, data storage devices and data storage media, in any standard, distributed or clustered environment. The application server 408 can include any appropriate hardware and software for integrating with the data store 410 as needed to execute aspects of one or more applications for the client device and handling a majority of the data access and business logic for an application. The application server provides access control services in cooperation with the data store and is able to generate content such as text, graphics, audio and/or video to be transferred to the user, which may be served to the user by the Web server 406 in the form of HTML, XML or another appropriate structured language in this example. The handling of all requests and responses, as well as the delivery of content between the client device 402 and the application server 408, can be handled by the Web server 406. It should be understood that the Web and application servers are not required and are merely example components, as structured code discussed herein can be executed on any appropriate device or host machine as discussed elsewhere herein.

The data store 410 can include several separate data tables, databases, or other data storage mechanisms and media for storing data relating to a particular aspect. For example, the data store illustrated includes mechanisms for storing content (e.g., production data) 412 and user information 416, which can be used to serve content for the production side. The data store is also shown to include a mechanism for storing log or session data 414. It should be understood that there can be many other aspects that may need to be stored in the data store, such as page image information and access rights information, which can be stored in any of the above listed mechanisms as appropriate or in additional mechanisms in the data store 410. The data store 410 is operable, through logic associated therewith, to receive instructions from the application server 408 and obtain, update or otherwise process data in response thereto. In one example, a user might submit a search request for a certain type of item and/or information. In this case, the data store might access the user information to verify the identity of the user and can access a catalog of sorts to obtain information about items of that type, such as a golf round score or handicap. The information can then be returned to the user, such as in a results listing on a Web page that the user is able to view via a browser on the user device 402. Information for a particular item of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 4. Thus, the depiction of the system 400 in FIG. 4 should be taken as being illustrative in nature and not limiting to the scope of the disclosure.

The various embodiments can be further implemented in a wide variety of operating environments, which in some cases can include one or more user computers or computing devices which can be used to operate any of a number of applications. Again, user or client devices 402 can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, gaming systems, and other devices capable of communicating via a network.

Most embodiments utilize at least one network 404 that would be familiar to those skilled in the art for supporting communications using any of a variety of commercially-available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM®.

The environment 400 can include a variety of data stores 410 and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch-sensitive display element, or keypad) and at least one output device (e.g., a display device, printer, or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and other non-transitory computer readable media for containing code, or portions of code, can include any appropriate media known or used in the art, such as, but not limited to, volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk ("DVD") or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative, rather than a restrictive, sense. And it will be evident that various modifications and changes may be made thereunto without departing from the broader spirit and scope of the invention as set forth in the claims.

What is claimed is:

1. A computer-implemented method, comprising:
   under control of one or more computer systems configured with executable instructions,
   receiving, from at least one client computing device or at least one golfing club computing device, historical performance data from a plurality of rounds for individual golfers of a plurality of golfers, the historical performance data including at least scoring data and handicap data for the plurality of golfers;
   receiving, from at least one different client computing device or the at least one golfing club computing device, confirmation of the accuracy of the historical performance data from one or more rounds of the plurality of rounds for one or more of the individual golfers of the plurality of golfers, wherein the confirmation is provided by one or more other individual golfers of the plurality of golfers that were present at each round for which they provide confirmation;
   determining, by a trained model and based at least in part on the historical performance data, whether the scoring data for the individual golfers satisfies a plurality of rules requiring accurately reported scoring data to identify purposeful influence of the handicap data by the individual golfers, at least two or more rules of the plurality of rules are weighted differently, wherein the plurality of rules are used to indicate whether the scoring data for the individual golfers is reported accurately by including at least:
      manipulation, based on a first set of data types and fields, of a plurality of individual rounds of the historical performance data for the individual golfers to identify inconsistencies,
      manipulation, based on a second set of data types and fields, of subsets of the historical performance data for the individual golfers to similar subsets of the historical performance data for subsets of the plurality of golfers to identify inconsistencies,
      manipulation of the historical performance data for the individual golfers to identify occurrences of unreceived rounds, and
      manipulation of the historical performance data for the individual golfers to identify occurrences of unreceived round confirmations;
   identifying, by the trained model and based at least in part on the historical performance data and the plurality of rules, that the scoring data for at least one golfer of the plurality of golfers does not satisfy one or more rules of the plurality of rules requiring accurately reported scoring data to identify purposeful influence of the handicap data by the individual golfers;

generating, by the trained model and based at least in part on the handicap data and the plurality of rules, an updated handicap for the at least one golfer to at least partially compensate for the scoring data that does not satisfy the one or more rules; and causing the updated handicap to be presented on a display of at least one of the client computing device or the golfing club computing device.

2. The computer-implemented method of claim 1, further comprising:

developing the trained model via training a neural network using a sample data set, the sample data set including information associated with golf scoring and golf handicaps; and applying the trained model to determine an accuracy likelihood for a new golf handicap or a new round score for the at least one golfer.

3. The computer-implemented method of claim 2, wherein the accuracy likelihood is based at least in part on one or more of the historical performance data, application of the trained model, or the plurality of rules.

4. The computer-implemented method of claim 1, further comprising:

generating, by the trained model, an overall adjusted score for each player in a party, the party including the at least one golfer.

5. The computer-implemented method of claim 1, wherein the historical performance data is shared with one or more third-parties, the one or more third-parties including at least one of a partner of the at least one golfer or a golfing club where the at least one golfer played a round of golf.

6. The computer-implemented method of claim 1, further comprising:

identifying at least one of a time or a time period where a new golf round score is expected to be submitted for the at least one golfer; and verifying that the new golf round score was submitted to at least one of client computing device or the golfing club computing device.

7. A system, comprising:

at least one processor, and memory including instructions that, when executed by the at least one processor, cause the system to:

receive, from at least one client computing device or at least one golfing club computing device, historical performance data from a plurality of rounds for individual golfers of a plurality of golfers, the historical performance data including at least scoring data and handicap data for the plurality of golfers;

receive, from at least one different client computing device or the at least one golfing club computing device, confirmation of the accuracy of the historical performance data from one or more rounds of the plurality of rounds for one or more of the individual golfers of the plurality of golfers, wherein the confirmation is provided by one or more other individual golfers of the plurality of golfers that were present at each round for which they provide confirmation;

determine, by a trained model and based at least in part on the historical performance data, whether the scoring data for the individual golfers satisfies a plurality of rules requiring accurately reported scoring data to identify purposeful influence of the handicap data by the individual golfers, at least two or more rules of the plurality of rules are weighted differently, wherein the plurality of rules are used to indicate whether the scoring data for the individual golfers is reported accurately by including at least:

manipulation, based on a first set of data types and fields, of a plurality of individual rounds of the historical performance data for the individual golfers to identify inconsistencies, manipulation, based on a second set of data types and fields, of subsets of the historical performance data for the individual golfers to similar subsets of the historical performance data for subsets of the plurality of golfers to identify inconsistencies, manipulation of the historical performance data for the individual golfers to identify occurrences of unreceived rounds, and manipulation of the historical performance data for the individual golfers to identify occurrences of unreceived round confirmations;

identify, by the trained model and based at least in part on the historical performance data and the plurality of rules, that the scoring data for at least one golfer of the plurality of golfers does not satisfy one or more rules of the plurality of rules requiring accurately reported scoring data to identify purposeful influence of the handicap data by the individual golfers;

generate, by the trained model and based at least in part on the handicap data and the plurality of rules, an updated handicap for the at least one golfer to at least partially compensate for the scoring data that does not satisfy the one or more rules; and cause the updated handicap to be presented on a display of at least one of the client computing device or the golfing club computing device.

8. The system of claim 7, wherein the instructions when executed by the at least one processor, further cause the system to:

develop the trained model via training a neural network using a sample data set, the sample data set including information associated with golf scoring and golf handicaps; and apply the trained model to determine an accuracy likelihood for a new golf handicap or a new round score for the at least one golfer.

9. The system of claim 8, wherein the accuracy likelihood is based at least in part on one or more of the historical performance data, application of the trained model, or the plurality of rules.

10. The system of claim 7, wherein the instructions when executed by the at least one processor, further cause the system to:

generate, by the trained model, an overall adjusted score for each player in a party, the party including the at least one golfer.

11. The system of claim 7, wherein the historical performance data is shared with one or more third-parties, the one or more third-parties including at least one of a partner of the at least one golfer or a golfing club where the at least one golfer played a round of golf.

12. The system of claim 7, wherein the instructions when executed by the at least one processor, further cause the system to:

identify at least one of a time or a time period where ta new golf round score is expected to be submitted for the at least one golfer; and verify that the new golf round score was submitted to at least one of client computing device or the golfing club computing device.

13. The system of claim 7, wherein the instructions when executed by the at least one processor, further cause the system to:

track, based at least in part on geolocation data, a golf round status for the at least one golfer.

14. A non-transitory computer-readable storage medium storing instructions that, when executed by at least one processor of a computing device, further cause the computing device to:

receive, from at least one client computing device or at least one golfing club computing device, historical performance data from a plurality of rounds for individual golfers of a plurality of golfers, the historical performance data including at least scoring data and handicap data for the plurality of golfers;

receive, from at least one different client computing device or the at least one golfing club computing device, confirmation of the accuracy of the historical performance data from one or more rounds of the plurality of rounds for one or more of the individual golfers of the plurality of golfers, wherein the confirmation is provided by one or more other individual golfers of the plurality of golfers that were present at each round for which they provide confirmation;

determine, by a trained model and based at least in part on the historical performance data, whether the scoring data for the individual golfers satisfies a plurality of rules requiring accurately reported scoring data to identify purposeful influence of the handicap data by the individual golfers, at least two or more rules of the plurality of rules are weighted differently, wherein the plurality of rules are used to indicate whether the scoring data for the individual golfers is reported accurately by including at least:

manipulation, based on a first set of data types and fields, of a plurality of individual rounds of the historical performance data for the individual golfers to identify inconsistencies, manipulation, based on a second set of data types and fields, of subsets of the historical performance data for the individual golfers to similar subsets of the historical performance data for subsets of the plurality of golfers to identify inconsistencies, manipulation of the historical performance data for the individual golfers to identify occurrences of unreceived rounds, and manipulation of the historical performance data for the individual golfers to identify occurrences of unreceived round confirmations;

identify, by the trained model and based at least in part on the historical performance data and the plurality of rules, that the scoring data for at least one golfer of the plurality of golfers does not satisfy one or more rules of the plurality of rules requiring accurately reported scoring data to identify purposeful influence of the handicap data by the individual golfers;

generate, by the trained model and based at least in part on the handicap data and the plurality of rules, an updated handicap for the at least one golfer to at least at least partially compensate for the scoring data that does not satisfy the one or more rules; and cause the updated handicap to be presented on a display of at least one of the client computing device or the golfing club computing device.

15. The non-transitory computer-readable storage medium of claim 14, wherein the instructions, when executed, further cause the computing device to:

develop the trained model via training a neural network using a sample data set, the sample data set including information associated with golf scoring and golf handicaps; and apply the trained model to determine an accuracy likelihood for a new golf handicap or a new round score for the at least one golfer.

16. The non-transitory computer-readable storage medium of claim 15, wherein the accuracy likelihood is based at least in part on one or more of the historical performance data, application of the trained model, or the plurality of rules.

17. The non-transitory computer-readable storage medium of claim 14, wherein the instructions, when executed, further cause the computing device to:

generate, by the trained model, an overall adjusted score for each player in a party, the party including the at least one golfer.

18. The non-transitory computer-readable storage medium of claim 14, wherein the historical performance data is shared with one or more third-parties, the one or more third-parties including at least one of a partner of the at least one golfer or a golfing club where the at least one golfer played a round of golf.

19. The non-transitory computer-readable storage medium of claim 14, wherein the instructions, when executed, further cause the computing device to:

identify at least one of a time or a time period where a new golf round score is expected to be submitted for the at least one golfer; and verify that the new golf round score was submitted to at least one of client computing device or the golfing club computing device.

20. The non-transitory computer-readable storage medium of claim 14, wherein the instructions, when executed, further cause the computing device to track, based at least in part on geolocation data, a golf round status for the at least one golfer.

* * * * *